(12) United States Patent
Cox et al.

(10) Patent No.: US 11,096,873 B2
(45) Date of Patent: Aug. 24, 2021

(54) HAIR CARE PRODUCT AND PROCESS FOR HAIR CARING

(71) Applicant: Henkel AG & Co. KGaA, Duesseldorf (DE)

(72) Inventors: Bruce R. Cox, Shanghai (CN); Yi hua Jiang, Shanghai (CN); Xiao wei Chang, Shanghai (CN)

(*) Notice: Subject to any disclaimer, the term of this patent is extended or adjusted under 35 U.S.C. 154(b) by 774 days.

(21) Appl. No.: 15/317,831

(22) PCT Filed: Jun. 11, 2014

(86) PCT No.: PCT/CN2014/079657
§ 371 (c)(1),
(2) Date: Dec. 9, 2016

(87) PCT Pub. No.: WO2015/188325
PCT Pub. Date: Dec. 17, 2015

(65) Prior Publication Data
US 2017/0119632 A1 May 4, 2017

(51) Int. Cl.
| | | |
|---|---|---|
| *A61K 8/06* | (2006.01) | |
| *A61Q 5/12* | (2006.01) | |
| *A61K 8/891* | (2006.01) | |
| *A61K 8/41* | (2006.01) | |
| *A61Q 5/00* | (2006.01) | |
| *A61K 8/898* | (2006.01) | |
| *A61K 8/34* | (2006.01) | |
| *A61K 8/37* | (2006.01) | |
| *A61K 8/58* | (2006.01) | |
| *A61K 8/81* | (2006.01) | |

(52) U.S. Cl.
CPC .............. *A61K 8/062* (2013.01); *A61K 8/342* (2013.01); *A61K 8/37* (2013.01); *A61K 8/416* (2013.01); *A61K 8/585* (2013.01); *A61K 8/8152* (2013.01); *A61K 8/891* (2013.01); *A61K 8/898* (2013.01); *A61Q 5/00* (2013.01); *A61Q 5/12* (2013.01); *A61K 2800/48* (2013.01); *A61K 2800/592* (2013.01); *A61K 2800/596* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 5,616,331 A | * | 4/1997 | Allard .................. | A61K 8/0204 424/401 |
| 6,726,729 B2 | * | 4/2004 | Patel ...................... | A61K 8/411 8/405 |
| 2008/0260673 A1 | * | 10/2008 | Hoffmann ............ | A61K 8/8152 424/70.9 |
| 2009/0185994 A1 | * | 7/2009 | Bistram .................. | A61K 8/39 424/70.11 |
| 2010/0254924 A1 | | 10/2010 | Hamilton et al. | |
| 2013/0305463 A1 | * | 11/2013 | Uellner .................... | A61K 8/41 8/406 |

FOREIGN PATENT DOCUMENTS

| | | | | |
|---|---|---|---|---|
| CN | 101433501 A | | 5/2009 | |
| FR | 3004645 A1 | | 10/2014 | |
| JP | 201287075 | * | 5/2012 | ............... A61K 8/41 |
| WO | 9609030 A1 | | 3/1996 | |
| WO | 2006063104 A2 | | 6/2006 | |
| WO | 2012025615 A2 | | 3/2012 | |
| WO | 2014000952 A2 | | 1/2014 | |

OTHER PUBLICATIONS

CIR Expert Panel, p. 1-45. http://www.cir-safety.org/sites/default/files/120_final_penttet.pdf. Published Sep. 2011.*
Dow Corning 245 Fluid. http://www.corquiven.com.ve/esp/PDS/SILICON_245_Fluid.pdf Published: 2003.*
JP201287075 Eng. Tran. Published: May 10, 2012.*
Umbach, W., et al. "Cosmetic-Preparations for Hair Care," Cosmetics and Toiletries, Development, Production and Use, 1991, p. 199.
State Intellectual Property Offfice of the P.R. China, International Search Report and Written Opinion issued in International Application No. PCT/CN2014/079657, dated Mar. 11, 2015.
Database GNPD [Online] MINTEL; Jan. 1, 2013; "Hair Care Kit"; XP002779061 Database accession No. 1973939.
Database GNPD [Online] MINTEL; Nov. 1, 2009; "Post-Hair Straightening Maintenance Kit"; XP002779062 Database accession No. 1209229.
Database GNPD [Online] MINTEL; Feb. 1, 2009; "3-Pack Trial Kit"; XP002779063 Database accession No. 1049530.

* cited by examiner

*Primary Examiner* — Nicole P Babson
*Assistant Examiner* — Lori K Mattison
(74) *Attorney, Agent, or Firm* — Lorenz & Kopf, LLP

(57) ABSTRACT

Disclosed herein is a hair care product is provided, which comprises an oil-in-water emulsion A and an oil-in-water emulsion C, wherein emulsion A has a pH-value from greater than 7.0 to 12.0 and contains: a1) at least one cationic surfactant A, and a2) at least one amino-functionalized silicone A; and emulsion C has a pH-value from 2.0 to lower than 7.0, and contains: c1) at least one cationic surfactant C, wherein surfactant A and surfactant C may be identical with or different from each other, and c2) at least one silicone C, wherein silicone C and the amino-functionalized silicone A may be identical with or different from each other, wherein emulsion A and emulsion C are separated from each other before use. Also disclosed herein is a process for hair caring by using the hair care product as contemplated herein.

6 Claims, 1 Drawing Sheet

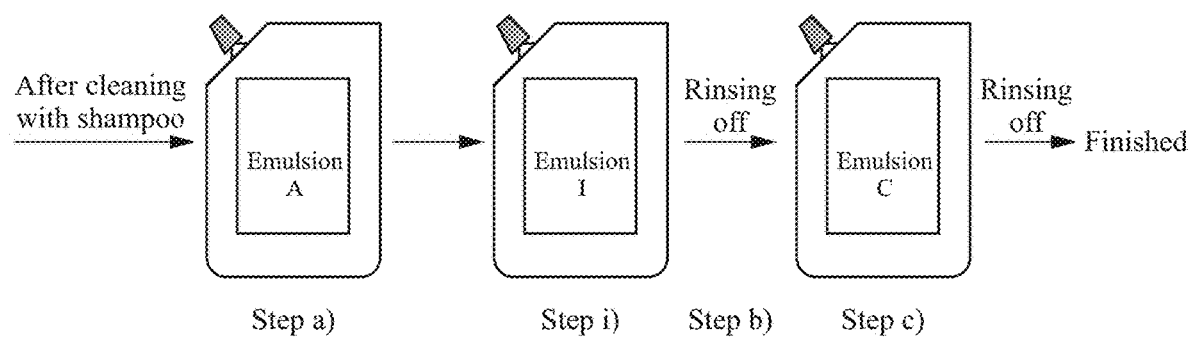

HAIR CARE PRODUCT AND PROCESS FOR HAIR CARING

CROSS-REFERENCE TO RELATED APPLICATION

This application is a U.S. National-Stage entry under 35 U.S.C. § 371 based on International Application No. PCT/CN2014/079657, filed Jun. 11, 2014 which was published under PCT Article 21(2), which is hereby incorporated in its entirety by reference.

FIELD OF THE INVENTION

The present disclosure relates to a hair care product and a process for hair caring by using the same.

BACKGROUND

Environmental influences (such as heat, sun and wind) as well as repeated hair treatment (such as coloring, bleaching and perming) make the hair sensitive and fragile. As a result, damaged cuticles spread out and expand, leaving the cortex exposed. Therefore, there is an increasing demand for hair caring products and processes to repair damaged hair, especially to condition highly-damaged Asian hair which is naturally straight and stiff.

Processes for hair treatment are known that include: applying to the hair an alkaline composition including one or more reducing agents in a cosmetically acceptable medium, rinsing the hair, and then applying to the hair a composition with an acidic pH containing one or more ceramides in a cosmetically acceptable medium, and finally rinsing the hair again.

Processes for treating hair are also known which applies the following compositions to the hair in sequence: a slightly alkaline aqueous composition; a composition comprising quaternized hydrolyzed keratins, hydrolyzed keratins and keratin amino acids; and a shampooing composition comprising a cationic surfactant and having a slightly acidic pH. However, this process is aimed to shampooing hair instead of providing after-shampoo hair care. In addition, the compositions as used in this document require relatively long retention time and high temperature, which is time-consuming, laborious and inconvenient.

It has been proposed that after using soaps to wash the hair, acidic formulas are utilized as an after-wash treatment so as to remove soap films and smooth the surface of the hair. However, this method still encounters with static problems, especially in cold and dry weather.

Thus, there is still a demand for a product and a process to condition highly damaged hair and impart desirable properties such as antistatic control, softness, smoothness and moisture to dry hair.

BRIEF SUMMARY

Hair care products and processes for hair caring are provided herein. In an embodiment, a hair care product includes an oil-in-water emulsion A. Emulsion A has a pH-value from greater than about 7.0 to about 12.0. Emulsion A includes a1) at least one cationic surfactant A and a2) at least one amino-functionalized silicone A. The hair care product further includes an oil-in-water emulsion C. Emulsion C has a pH-value from about 2.0 to lower than about 7.0. Emulsion C includes c1) at least one cationic surfactant C. Surfactant A and surfactant C may be identical with or different from each other. Emulsion C further includes c2) at least one silicone C. Silicone C and the amino-functionalized silicone A may be identical with or different from each other. Emulsion A and emulsion C are separated from each other before use.

In another embodiment, a process for hair caring includes the following steps in sequence: step a) applying an oil-in-water emulsion A to the hair, step b) washing the hair, and step c) applying an oil-in-water emulsion C to the hair. Emulsion A has a pH-value from greater than about 7.0 to about 12.0. Emulsion A includes a1) at least one cationic surfactant A and a2) at least one amino-functionalized silicone A. Emulsion C has a pH-value from about 2.0 to lower than about 7.0. Emulsion C includes c1) at least one cationic surfactant C. Surfactant A and surfactant C may be identical with or different from each other. Emulsion C further includes c2) at least one silicone C. Silicone C and the amino-functionalized silicone A may be identical with or different from each other.

BRIEF DESCRIPTION OF THE DRAWINGS

The various embodiments will hereinafter be described in conjunction with the following drawing FIGURES, wherein like numerals denote like elements.

The FIG. shows a schematic view of the hair caring process according to one embodiment as contemplated herein.

DETAILED DESCRIPTION

The following detailed description is merely exemplary in nature and is not intended to limit the hair care products and methods for treating caring. Furthermore, there is no intention to be bound by any theory presented in the preceding background or the following detailed description.

Throughout this disclosure, all the scientific and technical terms, unless otherwise indicated, shall have the same meanings as those known to a person skilled in the art. Where there is inconsistency, the definition provided in the present invention should be taken.

Unless otherwise specified, all the percentages, parts, and ratios in this context are on the basis of weight of each emulsion.

Unless otherwise specified, every numerical range in this context intends to include both endpoints and any numbers and subranges falling within said numerical ranges.

All the materials, processes and examples are presented for the purposes of illustration, and therefore, unless expressly specified otherwise, are not construed as limitations as contemplated herein.

Generally, chemical composition and component content of the materials used in hair care field, especially the materials manufactured on industrial scale, usually intend to represent essential components and approximate amounts thereof, therefore allow the presence of error tolerances.

Herein, the term "comprising" means that other steps and other ingredients which do not affect the final effect can be included. This term encompasses the terms "consisting of" and "consisting essentially of". The product and process as contemplated herein can comprise, consist of, and consist essentially of the essential technical features and/or limitations of the invention described herein, as well as any additional and/or optional ingredients, components, steps, or limitations described herein.

Herein, the numbers or letters which are used to distinguish the components and steps from each other (A, C, I; a, b, c; a1, a2, c1, c2, i1, i2; or whatever) does not in itself imply any particular sequence of carrying out the steps.

Herein, the term "dimethicone" means dimethylpolysiloxane or polydimethylsiloxane, which is commonly known as a type of silicone oil (polymerized silicone).

Herein, the term "amodimethicone" means a silicone polymer end blocked with amino functional groups.

The various embodiments are described in detail as follows.

A novel after-shampoo hair care product and a multi-step process for hair caring are proposed herein. It was found that the product and the process as contemplated herein beneficially repair and renew highly damaged hair (for example, after perming and coloration), restoring hair moisture, smoothing hair cuticles, leaving the hair feeling soft and silky with a shiny look.

In one embodiment as contemplated herein, a hair care product is provided, which comprises an oil-in-water emulsion A and an oil-in-water emulsion C, wherein emulsion A has a pH-value from greater than about 7.0 to about 12.0, preferably from about 7.5 to about 9.8, and contains:
  a1) at least one cationic surfactant A, and
  a2) at least one amino-functionalized silicone A; and
emulsion C has a pH-value from about 2.0 to lower than about 7.0, preferably from about 3.0 to about 5.5, and contains:
  c1) at least one cationic surfactant C, wherein surfactant A and surfactant C may be identical with or different from each other, and
  c2) at least one silicone C, wherein silicone C and the amino-functionalized silicone A may be identical with or different from each other,
wherein emulsion A and emulsion C are separated from each other before use.

In another embodiment as contemplated herein, A process for hair caring by using the hair care product as contemplated herein, which comprises the following steps in sequence:
  step a) applying emulsion A to the hair,
  step b) washing the hair, and
  step c) applying emulsion C to the hair.
Optionally, step i) is carried out between step a) and step b): applying an additional component to the hair.

Optionally, the hair is washed after step c).

It has been found that the product and the process as contemplated herein are convenient to use or carry out at home or in beauty shops such as hair salons, and significantly improve the hair properties and ensure good compatibility, for example, by imparting desirable antistatic control, softness, smoothness and moisture to dry hair.

These and other features, aspects and advantages as contemplated herein will become evident to those skilled in the art from the following description of preferred embodiments taken in conjunction with the accompanying drawing.

Hair Care Product

The hair care product as contemplated herein comprises at least an alkaline oil-in-water emulsion A and an acidic oil-in-water emulsion C, wherein emulsion A and emulsion C are separated from each other before use, distinguishing the subject hair care product from the commercially available hair care products which generally take the form of uniform compositions whose pH values are unique, either acidic, or alkaline or neutral.

Specifically, the pH value of emulsion A is in an alkaline range, preferably in a weakly alkaline range, so as to open the hair cuticle and enable the hair conditioning components to penetrate deeply into the hair cortex. The pH value of emulsion C is in an acidic range, preferably in a weakly acidic range, so as to close the hair cuticle and lock in the hair conditioning components and moisture. Therefore, the product as contemplated herein can significantly improve the hair conditioning effects when compared with the commercially available hare care products which have similar components.

Emulsion A

The oil-in-water emulsion A has a pH-value from greater than about 7.0 to about 12.0, preferably from about 7.5 to about 9.8, and contains: a1) at least one cationic surfactant A, and a2) at least one amino-functionalized silicone A.

Preferably, emulsion A further contains at least one thickener and/or at least one emollient, more preferably contains both thickener and emollient at the same time.

Emulsion A may also comprise various additives besides the above-mentioned components a1, component a2, thickener and emollient, when necessary. The balance of emulsion A may be water, especially mineral water. The additives are commonly-known in the hair care or personal care field, and their contents can be appropriately adjusted according to actual requirements. Non-limiting examples of the additives include preservative, humectant, plant extract, hair fixative, stabilizer, hair dye and solvent which can impart desirable properties to the damaged hair, provided that the additives are chemically and physically compatible with the essential components of emulsion A, and do not otherwise unduly impair the product performance, aesthetics or stability of emulsion A.

Component a1): At Least One Cationic Surfactant A

Emulsion A as contemplated herein may comprise at least one cationic surfactant A. Cationic surfactant A may provide softness and antistatic effect to the hair. At the same time, cationic surfactant A also serves as an emulsifier and an antiseptic.

There is no specific limitation to cationic surfactant A used as contemplated herein, and those cationic surfactants which are known for use in hair care or other personal care may be used. Representative examples of cationic surfactant A include quaternary ammonium compounds, in particular quaternary ammonium halides, ester-quats and any combinations thereof.

Cationic surfactant A may be preferably selected from quaternary ammonium halides which have one to three $C_{12}$-$C_{22}$ alkyl, wherein halides include fluorides, chlorides, bromides and iodides. It is well-known that the more alkyl chains are contained in the molecules of quaternary ammonium halides, the better conditioning effects can be achieved. However, the surfactants become more expensive with the increase of the number of alkyl chains. Specific examples of cationic surfactant A include behentrimonium chloride, steartrimonium chloride, cetrimonium chloride, behentrimonium bromide, steartrimonium bromide, cetrimonium bromide and any combination thereof.

In emulsion A as contemplated herein, the aforementioned cationic surfactants may be used alone or in any combinations of two or more.

Emulsion A may comprise about 0.1 to about 10 wt.-% of component a1), preferably about 1-5 wt.-%, based on the total amount of 100 wt % emulsion A.

Component a2) at Least One Amino-Functionalized Silicone A

Emulsion A as contemplated herein may comprise at least one amino-functionalized silicone A. Component a2 contains at least one amino group and thus advantageously set emulsion A at the desired alkaline pH value without using additional pH adjusters. Of course, small amount of pH adjuster may also be appropriately added, if desired. In addition, the amino-functionalized silicone A may smooth the outer cuticle and make hair look smooth and glossy. In addition, the amino-functionalized silicone A also has an excellent affinity with hair.

Herein the term "amino-functionalized silicone" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of amino-functionalized silicone include amodimethicones and their derivatives, preferably selected from amodimethicones, Bis(C13-15 Alkoxy) PG Amodimethicones (i.e. bis(C13 to C15 alkoxy) propylene glycol amodimethicone), Bis-Hydroxy/Methoxy Amodimethicones, Aminopropyl phenyl trimethicones, Aminopropyl dimethicones, Bisamino PEG/PPG-41/3 Aminoethyl PG-Propyl Dimethicones (i.e. Bisamino polyethylene glycol/polypropylene glycol-41/3 Aminoethyl propylene glycol-Propyl Dimethicones), and Caprylyl Methicones and any combinations thereof. Amino-functionalized silicones may be, for example, commercially available products XF49-C1109-18K (manufacturer: MOMENTIVE) and XF-42-B1989 (manufacturer: MOMENTIVE).

In emulsion A as contemplated herein, the aforementioned amino-functionalized silicones may be used alone or in any combinations of two or more. Since most amodimethicones have high viscosities, they are usually dissolved in cyclomethicones (i.e. cyclic dimethicones) or dimethicones so as to form silicone mixtures before use or for sale. Alternatively, the amino-functionalized silicones may already be in the form of emulsions. The name of the amino-functionalized silicone intends to represent the essential component and involves deviation that is considered usual by the person skilled in the art, especially in connection with products manufactured in industry.

Emulsion A may comprise about 0.1 to about 20 wt.-%, preferably about 1.0 to about 10 wt.-% of component a2), based on the total amount of 100 wt % emulsion A.

Emulsion C

The oil-in-water emulsion C has a pH-value from about 2.0 to lower than about 7.0, preferably from about 3.0 to about 5.5, and contains c1) at least one cationic surfactant C, wherein surfactant A and surfactant C may be identical with or different from each other, and c2) at least one silicone C, wherein silicone C and the amino-functionalized silicone A may be identical with or different from each other.

Small amount of pH adjuster may be appropriately added to impart emulsion C an acidic pH value.

Preferably, emulsion C further contains at least one thickener and/or at least one emollient, more preferably contains both thickener and emollient at the same time.

Emulsion C may additionally comprise various additives besides the above-mentioned components a1, component a2, thickener and emollient, when necessary. The balance of emulsion C may be water, especially mineral water.

The species and requirements of the additional additives are identical with those identified above for emulsion A.

Component c1): At Least One Cationic Surfactant C

Emulsion C as contemplated herein may comprise at least one cationic surfactant C. Cationic surfactant C may provide softness and antistatic effect to hair. At the same, cationic surfactant C also serves as an emulsifier and an antiseptic.

The species and requirements of cationic surfactant C are identical with those identified above for cationic surfactant A. In the case where cationic surfactant C is different from cationic surfactant A, a combined effect of hair care can be achieved. In the case where cationic surfactant C is identical with cationic surfactant A, the preparation of the final hair product is convenient and cost-efficient.

In an embodiment as contemplated herein, the oil-in-water emulsion C comprises about 0.1 to about 10 wt.-%, preferably about 0.1 to about 5.0 wt.-% of component c1), based on the total amount of 100 wt % emulsion C.

Component c2) at Least One Silicone C

Emulsion C as contemplated herein may comprise at least one silicone C. Silicone C may smooth the outer cuticle and make hair look smooth and glossy.

Any silicone known in the art for use in hair care or personal care products may be used, so long as it is chemically and physically compatible with the essential components of emulsion C.

Since amino group tends to impart an alkaline pH value to the emulsion, component c2 preferably contains no amino groups. Alternatively, amino-functionalized silicone may also be used alone or in combination with silicones which contain no amino groups. In case where amino-functionalized silicone is contained in component c2, the pH value may be adjusted by using suitable pH adjuster in an appropriate amount.

Non-limiting examples of silicone C include dialkylpolysiloxanes; methylphenylpolysiloxanes; cyclic silicones; amino-, fatty acid-, alcohol-, polyether-, epoxy-, fluorine-, glycoside- and alkyl-modified silicone compounds; alkyloxylated silicones; their derivatives and any combinations thereof, preferably selected from dialkylpolysiloxanes, more preferably dimethicones (i.e. dimethylpolysiloxanes). Suitable silicones may be, for example, commercially available products Poly dimethylsiloxane 60000 cSt (manufacturer: Dow corning), KF-9008 (manufacturer: Shin-Etsu), DC 1501 (manufacturer: Dow corning) and Cyclomethicone (manufacturer: Dow corning).

In emulsion C as contemplated herein, the aforementioned silicones may be used alone or in any combinations of two or more. The name of the silicone intends to represent the essential component and involves deviation that is considered usual by the person skilled in the art, especially in connection with products manufactured in industry.

In an embodiment as contemplated herein, the oil-in-water emulsion C comprises about 0.1 to about 25 wt.-%, preferably about 0.1 to about 10 wt.-% of component c2), based on the total amount of 100 wt % emulsion C.

All of the emulsions contemplated herein are oil-in-water compositions which penetrate deeply into hair fibers and advantageously repair the hair upon coming into contact with hair. Thus, the product as contemplated herein allows not only restructuring and conditioning the outside of the hair to produce a softer feeling, but also repairing the inside portion of the hair.

In addition, the emulsions contemplated herein can penetrate and repair the hair at room temperature without heating, which is energy-saving and makes hair care convenient and applicable even at home.

Furthermore, these emulsions do not require a long retention time. They can be washed away after being kept on the hair for several seconds to several minutes, for example, about 0.5 to about 15 minutes, which makes the product and the process as contemplated herein efficient and easy-handling.

The product according to the present application is applied to the hair step by step after shampooing the hair and rinsing the hair clean. Therefore, it is unnecessary for the emulsions contemplated hereinto contain cleaning components.

Thickener

Any thickener known in the art for use in hair care or personal care products may be used. The thickener may enhance the viscosity of emulsion A so that emulsion A can be used as hair cream, hair mask or the like.

There is no specific limitation to the thickener which is optionally used as contemplated herein. Non-limiting examples of the thickeners include fatty alcohols, preferably C14-26 fatty alcohols, for example cetearyl alcohol; homopolymers of (meth)acrylic acid and (meth)acrylates, carbomer, (meth)acrylate crosspolymers, such as acrylates/C10-30 alkyl acrylate crosspolymer, sodium acrylates/C10-30 alkyl acrylate crosspolymer, acrylates/ethylhexyl acrylate crosspolymer; acrylates/ammonium methacrylate copolymer, acrylates/ceteth-20 itaconate copolymer, acrylates/dimethicone copolymer, acrylates/vinyl isodecanoate crosspolymer, sodium acrylates copolymer, sodium acrylate/sodium acryloyldimethyl taurate copolymer, hydroxyethyl acrylate/sodium acryloyldimethyl taurate copolymer, acrylamide/ammonium acrylate copolymer, acrylamide/sodium acryloyldimethyltaurate copolymer, acrylamidopropyltrimonium chloride/acrylates copolymer, ammonium acryloyldimethyltaurate/VP copolymer; starches and their derivatives, for example, degraded starches which are chemically-modified or physically-modified, in particular dextrins and maltodextrins; gelatins, such as gum arabic, agar-agar, ghatti gum, gellan gum; modified and non-modified celluloses; pullulan, curdlan, carrageenans, alginic acid, alginates, pectin, inulin, xanthan gum and mixtures of two or more of these substances.

In emulsion A as contemplated herein, the aforementioned thickeners may be used alone or in any combinations of two or more.

The amount of the thickener may be in the range of 0-20 wt.-%, preferably about 0.1-10 wt.-%, preferably about 1-6 wt.-%, based on the total amount of 100 wt % emulsion A.

The illustrative species, amount and requirements of the thickener used in emulsion C, if any, are the same as those identified above in emulsion A.

Emollient

Any emollient known in the art for use in hair care or personal care products may be used in emulsion A. The emollient may make the hair smooth.

There is no specific limitation to the emollient which is optionally used as contemplated herein. Examples of the emollients include, without limitation thereto, esters of C6-C22 fatty acids (e.g., tri-esters of glycerin and a mixture of linear and branched chain C10-C18 fatty acids having the INCI name: C10-18 TRIGLYCERIDES), fatty alcohols, alkoxylated fatty alcohols, silicone fluids (volatile and non-volatile), silicone copolyols, unsubstituted and substituted methyl polysiloxanes (e.g., dimethicone, cetyl dimethicone, bis-hydroxyethoxypropyl dimethicone), liquid hydrocarbons, (e.g., mineral oil), and the like.

Non-limiting examples of suitable emollients also include mineral oil having a viscosity in the range of about 50 to about 500 centipoise (cps), lanolin oil, coconut oil, cocoa butter, olive oil, almond oil, macadamia nut oil, aloe extracts such as aloe vera lipoquinone squalane, castor oil, polybutene, sweet almond oil, avocado oil, calophyllum oil, ricin oil, vitamin E acetate, linotenic alcohol, oleyl alcohol, the oil of cereal germs such as the oil of wheat germ, isopropyl palmitate, octyl palmitate, isopropyl myristate, Pentaerythrityl Tetraethylhexanoate, hexadecyl stearate, butyl stearate, decyl oleate, acetyl glycerides, the octanoates and benzoates of C12-C15 alcohols, the octanoates and decanoates of alcohols and polyalcohols of glycol and glyceryl, ricinoleates esters such as isopropyl adipate, hexyl laurate and octyl dodecanoate, dicaprylyl maleate, hydrogenated vegetable oil, phenyltrimethicone, jojoba oil, aloe vera extract.

In emulsion A as contemplated herein, the aforementioned emollients may be used alone or in any combinations of two or more.

The amount of the emollient may be in the range of 0-20 wt.-%, preferably about 0.01-15 wt.-%, more preferably about 0.1-10 wt.-%, based on the total amount of 100 wt % emulsion A.

The illustrative species, amount and requirements of the emollient used in emulsion C, if any, are the same as those identified above in emulsion A.

Preservative

Any preservative known in the art for use in hair care or personal care products may be used in Emulsion A. The preservative may prolong the shelf life of emulsion A.

There is no specific limitation to the preservative which is optionally used as contemplated herein. Non-limiting examples of the preservatives include 2-bromo-2-nitropropane-1,3-diol, 5-bromo-5-nitro-1,3-dioxane, 7-thylbicyclooxazolidine, alkyl(C12-C22) trimonium bromide (i.e. alkyl(C12-C22) trimethyl ammonium bromide) and chloride, benzalkonium chloride, bromide and saccharinate, benzyl alcohol, benzoic acid, its salts and esters, chloroacetamide, chlorobutanol, chlorophene, chloroxylenol, chlorphenesin, dmdm hydantoin (i.e. dimethylol dimethyl), diazolidinyl urea, imidazolidinyl urea, dichlorobenzyl alcohol, dimethyl oxazolidine, methylisothiazolinone, phenoxyethanol, phenoxyisopropanol, methylparaben, propylparaben, salicylic acid and its salts, 4-hydroxybenzoic acid and its salts and esters.

In emulsion A as contemplated herein, the aforementioned preservatives may be used alone or in any combinations of two or more.

The amount of the preservative may be in the range of 0-20 wt.-%, preferably about 0.01-10 wt.-%, more preferably about 0.1-2 wt.-%, based on the total amount of 100 wt % emulsion A.

The illustrative species, amount and requirements of the preservative used in emulsion C, if any, are the same as those identified above in emulsion A.

In one embodiment as contemplated herein, the thickener, emollient and preservative used in emulsion C, independent from each other, are identical with or different from the thickener, emollient and preservative used in emulsion A.

Optional Components of the Hair Care Product

In addition to emulsion A and emulsion C as mentioned above, the hair care product as contemplated herein may further comprise optional component which is separated from emulsion A and emulsion C before use, so as to enhance the hair conditioning effects. The additional component may be in the form of oil-in-water emulsion (for example, "emulsion I" as illustrated below), aqueous solution, spray, hair mousse, hair gel, hair wax etc.

Emulsion I as mentioned below serves solely to illustrate the composition, the applying method, and the advantageous effects of the optional components used as contemplated herein, which cannot be construed as any limitation of the subject concept.

Emulsion I emulsion I may have a pH-value between about 4.0 to about 9.0, preferably between about 5.5 to about 7.5, and contains: i1) at least one surfactant I, wherein surfactant A, surfactant C and surfactant I may be identical with or different from each other; and i2) at least one silicone I, wherein the amino-functionalized silicone A, silicone C and silicone I may be identical with or different from each other, wherein emulsion A, emulsion C and emulsion I are separated from each other before use.

Preferably, emulsion I further contains at least one thickener and/or at least one emollient, more preferably contains both thickener and emollient at the same time.

Emulsion I may additionally comprise various additives besides the above-mentioned components i1, component i2, thickener and emollient, when necessary. The balance of emulsion I may be water, especially mineral water.

The species and requirements of the additional additives are identical with those identified above for emulsion A.

Component i1): At Least One Surfactant I

Emulsion I as contemplated herein may comprise at least one surfactant I. Surfactant I may serves as emulsifier.

Any cationic, nonionic and amphoteric surfactant known in the art for use in hair care or personal care products may be employed as surfactant I, so long as it is chemically and physically compatible with the essential components of the hair care product as contemplated herein.

In an embodiment as contemplated herein, the oil-in-water emulsion I comprises from about 0.1 wt.-% to less than about 7.0 wt.-%, preferably from about 0.5 wt.-% to less than about 5.0 wt.-% of component i1, based on the total amount of 100 wt % emulsion I.

Component i2) at Least One Silicone I

Emulsion I as contemplated herein may comprise at least one silicone I. Silicone I may smooth the outer cuticle and make hair look smooth and glossy.

The illustrative species of silicone I used in emulsion I, if any, are the same as those used in emulsion C.

In an embodiment as contemplated herein, the oil-in-water emulsion C comprises about 0.1 to about 20 wt.-%, preferably about 0.5 to about 12.0 wt.-% of component i2), based on the total amount of 100 wt % emulsion I.

Thickener, Emollient and Preservative

The illustrative species and requirements of the thickener, emollient and preservative used in emulsion I, if any, are the same as those used in emulsion A. In one embodiment as contemplated herein, the thickener, emollient and preservative used in emulsion I, independent from each other, are identical with or different from the thickener, emollient and preservative used in emulsion A and emulsion C.

The amount of the thickener may be in the range of 0-10 wt.-%, preferably about 0.01-8 wt.-%, more preferably about 0.5-7 wt.-%, based on the total amount of 100 wt % emulsion I.

The amount of the emollient may be in the range of 0-20 wt.-%, preferably about 0.01-15 wt.-%, more preferably about 1-10 wt-%, based on the total amount of 100 wt % emulsion I.

The amount of the preservative may be in the range of 0-20 wt.-%, preferably about 0.01-10 wt.-%, more preferably about 0.1-2 wt-%, based on the total amount of 100 wt % emulsion I.

Preparing Method of Emulsion a, Emulsion C or Emulsion I

Take the preparation of emulsion A for example. The components of emulsion A are mixed together to form a uniform oil-in-water emulsion before use. There is no specific limitation to the addition sequence of each component. For example, the oil-soluble components, such as the thickener and the emollient, are mixed together while stirring and heating to form an oil phase. The water soluble components, such as component a1) and water, are mixed together while stirring and heating to form an aqueous phase. Subsequently, the oil phase is added to the aqueous phase with homogenizing so as to form a uniform emulsion. Finally, the resultant mixture is cooled down before adding the volatile components, such as component a2), to form emulsion A.

The illustrative example for the preparation of emulsion C and emulsion I are similar with that illustrated for emulsion A.

pH Adjusting Method

In emulsion A, the amino-functionalized silicone A contains at least one amino group and thus exhibits an alkaline pH. At the same time, cationic surfactant A such as quaternary ammonium halide generally exhibits a weakly acidic pH. Emulsion A as a whole can have a desirable alkaline pH value without using additional pH adjusters. Of course, small amount of pH adjuster may also be appropriately added, if desired.

In emulsion C, cationic surfactant C such as quaternary ammonium halide generally exhibits a weakly acidic pH, which can impart an acidic pH value to emulsion C without using additional pH adjusters. Of course, small amount of pH adjuster may also be appropriately added, if desired.

In emulsion I, in the case where a nonionic surfactant, which generally exhibits a neutral pH value, is used as surfactant I, emulsion I as a whole also has a neutral pH value. Of course, small amount of pH adjuster may also be appropriately added, if desired.

There is no specific limitation to the pH adjuster which is optionally used in each emulsion as contemplated herein. Any pH adjuster commonly used in hair care or personal care products may be used herein. Non-limiting examples of the pH adjuster include citric acid, lactic acid, sodium hydroxide, potassium hydroxide, monoethanolamine, triethanolamine, some amino acids, etc.

Kit of Parts

In one embodiment as contemplated herein, a kit of parts is employed to contain each of the oil-in-water emulsion A, oil-in-water emulsion C and optional oil-in-water emulsion I.

Preferably, the kit of parts is in the form of two or more individual containers. Herein, the individual containers can also be assembled or taken apart. Alternatively, the kit of parts takes the form of a casing with one or more baffles inserted therein to divide the casing into two or more separate containers.

There is no specific limitation to the material of the kit of parts, for example, plastic, glass, ceramic, metal, and paper etc, preferably plastic may be used to make the kit of parts used as contemplated herein. The shape of the kit of parts is commonly-known, such as jar, bottle, box and bag etc.

Each emulsion may be poured out from the kit of parts when use.

Process for Hair Caring

The process for hair caring as contemplated herein comprises the following steps:

step a) applying to the hair an oil-in-water emulsion A with a pH-value from greater than about 7.0 to about 12.0, preferably from about 7.5 to about 9.8, containing:
 a1) at least one cationic surfactant A,
 a2) at least one amino-functionalized silicone A,
step b) washing the hair, and step c) applying to the hair an oil-in-water emulsion C with a pH-value of about 2.0 to lower than about 7.0, preferably from about 3.0 to about 5.5, containing:
  c1) at least one cationic surfactant C, wherein surfactant A and surfactant C may be identical or different from each other, and
  c2) at least one silicone C, wherein amino-functionalized silicone A silicone C may be identical or different from each other.

Preferably, step i) is additionally included between step a) and step b): applying additional components to the hair.

Preferably, step i) is carried out by applying to the hair an oil-in-water emulsion I with a pH-value between about 4.0 to about 9.0, preferably between about 5.5 to about 7.5, containing:
  i1) at least one surfactant I, wherein surfactant A, surfactant C and surfactant I may be identical with or different from each other; and
  i2) at least one silicone I, wherein the amino-functionalized silicone A, silicone C and silicone I may be identical with or different from each other.

The FIG. shows an embodiment of the hair caring process as contemplated herein. In the FIG. after cleaning the hair with shampoo and draining the hair with a towel, emulsion A is applied around hair ends by hand and kept for about 0.5-5 minutes. Subsequently, emulsion I is applied from hair ends to hair mids by hand and kept for about 0.5-5 minutes, then it is rinsed off with water. Finally, emulsion C is applied from hair ends to hair mids by hand and kept for about 0.5-5 minutes, followed by rinsing off with water.

There is no specific limitation to the way of applying each emulsion as contemplated herein to the hair. For example, each emulsion may be applied to the hair directly by hand, or with a wide-toothed comb or brush, or by any other method commonly used to apply a hair conditioner to the hair.

Of course, these emulsions can be heated after being applied to the hair, if desired. After the application of each emulsion, the hair is optionally massaged so as to promote absorption. Other measures which are commonly used to repair hair and/or promote the adsorption of hair conditioner may also be used according to actual requirements.

Each step as described below may be repeated one or more times, if necessary.

Each emulsion may be applied throughout the whole hair from hair roots to hair ends, however, in order to prevent hair follicles from being blocked, it is preferred to keep the emulsions away from the scalp. For example, emulsion A, emulsion I and emulsion C are separately applied from hair mids to hair ends. Herein, the term "hair mid" intends to represent any area between hair roots to hair ends, preferably around the central portion of the hair.

step a) is carried out after the hair is cleaned with shampoo and rinsed with water. There is no specific limitation to the shampoo, which may be any commercially available shampoo with hair cleansing function.

Optionally, step i) is carried out between step a) and step b).

That's to say, step i) is conducted immediately after step a) so as to apply an additional component, for example, an emulsion with neutral pH value, to the hair.

Step b) may be carried out after step a) or after step i), if any, so as to wash the hair, preferably with water. Preferably, the hair is further drained so as to at least partially remove water from the hair, for example, by using a hair dryer or with certain water-absorbing materials such as a towel immediately after step b).

The hair is preferably washed after step c) so as to at least partially remove emulsion C from the hair.

There is no specific limitation to the amount of the hair care product used, which may be any amount according to the hair quality and hair length. For example, emulsion A and emulsion C may be used in an amount of about 15 g for medium-length hair, and in an amount of about 20 to about 30 g for long hair. Emulsion I may be used in an amount of about 5 g for medium-length hair, and in an amount of about 6 g to about 10 g for long hair. A preferred ratio of Emulsion A:Emulsion I:Emulsion C is about 3:1:3.

EXAMPLES

The various embodiments are described below in more detail by way of examples, wherein the specific operations, materials, contents, data and other conditions and details in the examples serve solely to illustrate the modes to carry out the various embodiments and advantageous effects thereof and do not represent any limitations of the subject concept.

Materials

| Materials | INCI name | Supplier | Function |
|---|---|---|---|
| Pentaerythrityl Tetraethylhexanoate | Pentaerythrityl Tetraethylhexanoate | BASF | emollient |
| Cetearyl Alcohol | Cetearyl Alcohol | BASF | thickener |
| Steartrimonium Bromide | Steartrimonium Bromide | Shanghai Yusheng Tech-Trade Co. Ltd | cationic surfactant |
| Methylparaben | Methylparaben | Kunshan Shuangyou Daily | preservative |
| XF49-C1109-18K | Amodimethicone, Cyclomethicone | MOMENTIVE | amino-functionalized silicone |
| XF-42-B1989 | Amodimethicone | MOMENTIVE | amino-functionalized silicone |
| Behentrimonium Chloride | Behentrimonium Chloride | Clariant | cationic surfactant |
| Steartrimonium Chloride | Steartrimonium Chloride | Clariant | cationic surfactant |
| Dehyquart A CA | Cetrimonium Chloride | BASF | cationic surfactant |
| Poly-dimethylsiloxane 60000 cSt | Dimethicone | Dow corning | silicone |
| KF-9008 | A mixture of Cyclomethicone and Dimethicone | Shin-Etsu | silicone |
| DC 1501 | A mixture of Cyclomethicone and Dimethiconol | Dow Corning | silicone |
| Cyclomethicone | Cyclomethicone | Dow corning | silicone |
| Phenoxyethanol | Phenoxyethanol | Dow | preservative |
| Ceteareth-20 | Ceteareth-20 | Croda | surfactant |
| Dow Corning 1503 Fluid | A mixture of Dimethicone and Dimethiconol | Dow Corning | silicone |
| Propylparaben | Propylparaben | Kunshan Shuangyou Daily | preservative |
| Simulgel EG | A mixture of Sodium Acrylate/ Acryloyldimethyl Taurate Copolymer, Isohexadecane, Polysorbate 80 | Seppic | thickener |

<Preparation of the Emulsions>

Preparation of Emulsion A 3 g pentaerythrityl tetraethylhexanoate and 5 g cetearyl alcohol were mixed together in a beaker while stirring by using a stirrer RW 28 basic (manufactured by IKA, speed: 300 rpm) and heating to 80° C. so as to form an oil phase. 4 g steartrimonium bromide, 80.3 g water and 0.2 g methylparaben were mixed together in another beaker while stirring by using a stirrer RW 28 basic (manufactured by IKA, speed: 300 rpm) and heating to 80° C. so as to form an aqueous phase. Subsequently, the oil phase was added to the aqueous phase while homogenizing by using a homogenizer L5T (manufactured by SILVERSON, speed: 4500 rpm) for 5 minutes so as to form a uniform emulsion. The resultant emulsion was cooled down to 60° C. Then 2 g XF49-C1109-18K and 5 g XF-42-B1989 were added to the emulsion with stirring. The resultant mixture was further cooled down to 45° C. Finally, 0.5 g phenoxyethanol was added to the mixture while stirring for 15 min to obtain emulsion A. The pH value of emulsion A was 9.0.

The formulation of emulsion A was as follows:

| Materials | Function |
| --- | --- |
| Pentaerythrityl Tetraethylhexanoate (3 g) | emollient |
| Cetearyl Alcohol (5 g) | thickener |
| Steartrimonium Bromide (4 g) | cationic surfactant |
| Water (80.3 g) | |
| Methylparaben (0.2 g) | preservative |
| XF49-C1109-18K (2 g) | amino-functionalized silicone |
| XF-42-B1989 (5 g) | amino-functionalized silicone |
| Phenoxyethanol (0.5 g) | preservative | pH value of emulsion A 9.0

Preparation of Emulsion C 3 g pentaerythrityl tetraethylhexanoate and 5 g cetearyl alcohol were mixed together in a beaker while stirring by using a stirrer RW 28 basic (manufactured by IKA, speed: 300 rpm) and heating to 80° C. so as to form an oil phase. 1 g behentrimonium chloride, 2 g steartrimonium chloride, 1 g Dehyquart A CA, 0.2 g methylparaben and 78.3 g water were mixed together in another beaker while stirring by using a stirrer RW 28 basic (manufactured by IKA, speed: 300 rpm) and heating to 80° C. so as to form an aqueous phase. Subsequently, the oil phase was added to the aqueous phase while homogenizing by using a homogenizer L5T (manufactured by SILVERSON, speed: 4500 rpm) for 5 minutes so as to form a uniform emulsion. The resultant emulsion was cooled down to 60° C. Then 2 g Polydimethylsiloxane 60000, 4 g KF-9008, 1 g DC 1501 and 2 g cyclomethicone were added to the emulsion with stirring. The resultant mixture was further cooled down to 45° C. Finally, 0.5 g phenoxyethanol was added to the mixture while stirring for 15 min to obtain emulsion C. The pH value of emulsion C was 4.2.

The formulation of emulsion C was as follows:

| Materials | Function |
| --- | --- |
| Pentaerythrityl Tetraethylhexanoate (3 g) | emollient |
| Cetearyl Alcohol (5 g) | thickener |
| Behentrimonium Chloride (1 g) | cationic surfactant |
| Steartrimonium Chloride (2 g) | cationic surfactant |
| Dehyquart A CA (1 g) | cationic surfactant |
| Methylparaben (0.2 g) | preservative |
| Water (78.3 g) | |
| Polydimethylsiloxane 60000 cSt (2 g) | silicone |
| KF-9008 (4 g) | silicone |
| DC 1501 (1 g) | silicone |
| Cyclomethicone (2 g) | silicone |
| Phenoxyethanol (0.5 g) | preservative | pH value of emulsion C 4.2

Preparation of Emulsion I 5 g pentaerythrityl tetraethylhexanoate, 2.5 g cetearyl alcohol, 0.8 g ceteareth-20 and 0.2 g propylparaben were mixed together in a beaker while stirring by using a stirrer RW 28 basic (manufactured by IKA, speed: 300 rpm) and heating to 80° C. so as to form an oil phase. 83.3 g water and 0.2 g methylparaben were mixed together in another beaker while stirring by using a stirrer RW 28 basic (manufactured by IKA, speed: 300 rpm) and heating to 80° C. so as to form an aqueous phase. Subsequently, the oil phase was added to the aqueous phase while homogenizing by using a homogenizer L5T (manufactured by SILVERSON, speed: 4500 rpm) for 5 minutes so as to form a uniform emulsion. The resultant emulsion was cooled down to 60° C. Then 4 g Dow Corning 1503 Fluid, 3 g polydimethylsiloxane 60000 and 0.5 g Simulgel EG were added to the emulsion with stirring. The resultant mixture was further cooled down to 45° C. Finally, 0.5 g phenoxyethanol was added to the mixture while stirring for 15 min to obtain emulsion I. The pH value of emulsion I was 6.7.

The formulation of emulsion I was as follows:

| Materials | Function |
| --- | --- |
| Pentaerythrityl Tetraethylhexanoate (5 g) | emollient |
| Cetearyl Alcohol (2.5 g) | thickener |
| Ceteareth-20 (0.8 g) | surfactant |
| Propylparaben (0.2 g) | preservative |
| Water (83.3 g) | |
| Methylparaben (0.2 g) | preservative |
| Dow Corning 1503 Fluid (4 g) | silicone |
| Polydimethylsiloxane 60000 cSt (3 g) | silicone |
| Simulgel EG (0.5 g) | thickener |
| Phenoxyethanol (0.5 g) | preservative | pH value of emulsion I 6.7

<Test Methods>

Eight Chinese women with medium-length hair participated in the tests as volunteers. The eight volunteers' hair was shampooed, rinsed off with water and dried with towels. Then, the hair care product as contemplated herein was applied to the left side of volunteers' hair, and a commercially available hair care product (Name: One step Treatment Salon only TL (hereinafter referred to as "TL"), Brand: Schwarzkopf professional, Manufactory: Henkel Japan) was applied to the right side of their hair (also known as half-head test).

The formulation of TL was as follows:

| Materials | Function |
| --- | --- |
| Cetearyl Alcohol | thickener |
| Dicaprylyl Carbonate | emollient |
| Glycol Distearate | emollient |
| Behentrimonium Chloride | cationic surfactant |

-continued

| Materials | Function |
|---|---|
| Distearoylethyl Hydroxyethylmonium Methosulfate | cationic surfactant |
| Dimethicone | silicone |
| Phenoxyethanol | preservative |
| Methylparaben | preservative | pH value of TL 3.2

Example 1 and Comparative Example 1

7.5 g emulsion A as obtained above was applied to the left side of hair and kept for 0.5 min, and rinsed off with water. Then 7.5 g emulsion C as obtained above was applied to the left side of hair and kept for 0.5 min, and rinsed off with water again.

7.5 g TL was applied to the right sides of the eight volunteers' hair and kept for 0.5 min, then rinsed off with water.

Example 2 and Comparative Example 2

7.5 g emulsion A as obtained above was applied to the left side of hair and kept for 0.5 min, then 2.5 g emulsion I was applied to the left side of hair and kept for 0.5 min, and rinsed off with water. Finally, 7.5 g emulsion C as obtained above was applied to the left side of hair and kept for 0.5 min, and rinsed off with water again.

7.5 g TL was applied to the right sides of the eight volunteers' hair and kept for 0.5 min, then rinsed off with water.

<Test Results>

A team of well-trained hair dressers of Henkel salon team assessed the hair care results and scored every volunteer on a scale of 1 to 5. The scores for the eight volunteers given by the hair dresser team were averaged and recorded in the following tables.

5: Good,
4: Slightly good,
3: Slightly bad,
2: Bad, and
1: Very bad.

TABLE 1 test results of Example 1 vs. Comparative Example 1

|  | Example 1 | Comparative Example 1 |
|---|---|---|
| moisture of dry hair ends | 4.57 | 4.00 |
| softness of dry hair | 4.71 | 4.00 |
| smoothness of dry hair | 5.00 | 4.14 |
| Static/electricity control | 4.57 | 4.29 |
| combability after drying | 4.86 | 3.86 |
| look of dry hair, not flying away | 4.71 | 4.14 |

TABLE 2 test results of Example 2 vs. Comparative Example 2

|  | Example 2 | Comparative Example 2 |
|---|---|---|
| moisture of dry hair ends | 4.57 | 3.86 |
| softness of dry hair | 4.57 | 3.71 |
| smoothness of dry hair | 4.86 | 3.86 |
| static/electricity control | 4.86 | 4.43 |
| combability after drying | 4.86 | 3.71 |
| look of dry hair, not flying away | 4.86 | 3.71 |

It can be clearly seen from Table 1 and Table 2 that when comparing with the commercially available product which was applied in one step, the products as contemplated herein which were applied in two or three steps exhibited excellent hair-caring effects on highly-damaged hair and impart desirable properties such as antistatic control, softness, smoothness and moisture to dry hair.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment. It being understood that various changes may be made in the function and arrangement of elements described in an exemplary embodiment without departing from the scope of the subject matter as set forth in the appended claims.

What is claimed is:

1. A hair care product comprising:
    an oil-in-water emulsion A, wherein emulsion A has a pH-value from greater than about 7.0 to about 12.0 and comprises:
        a1) steartrimonium bromide, and
        a2) amodimethicone;
    an oil-in-water emulsion I, wherein emulsion I has a pH-value from about 4.0 to about 9.0 and comprises:
        i1) at least one surfactant I, and
        i2) at least one silicone I, and
    an oil-in-water emulsion C, wherein emulsion C has a pH-value from about 2.0 to lower than about 7.0 and comprises:
        c1) bentrimonium chloride, wherein the at least one surfactant I may be identical with or different from a1) and c1), and
        c2) a mixture of dimethicone and cyclopentasiloxane,
    wherein the at least one-silicone I may be identical with or different from a2) and c2),
    wherein emulsion A, emulsion I, and emulsion C are non-leave-on emulsions, and
    wherein emulsion A, emulsion I, and emulsion C are provided in separate containers.

2. The hair care product according to claim 1, wherein emulsion A comprises:
    about 0.1 to about 10.0 wt._% of a1) steartrimonium bromide, and about 0.1 to about 20 wt._% of a2) amodimethicone, based on the total amount of 100 wt % emulsion A.

3. The hair care product according to claim 1, wherein emulsion C comprises:
about 0.1 to about 10 wt._% of c1) bentrimonium chloride, and
about 0.1 to about 25 wt._% of c2) the mixture of dimethicone and cyclopentasiloxane,
based on the total amount of 100 wt_% emulsion C.

4. The hair care product according to claim 1, wherein emulsion A, emulsion C, or both emulsion A or emulsion C, further comprise pentaerythrityl tetraethylhexanoate and optionally cetearyl alcohol or.

5. The hair care product according to claim 1, wherein:
emulsion A comprises:
about 0.1 to about 10.0 wt._% of a1) steartrimonium bromide, and
about 0.1 to about 20 wt._% of a2) amodimethicone, based on the total amount of 100 wt._% emulsion A; and
emulsion C comprises:
about 0.1 to about 10 wt._% of c1) bentrimonium chloride, and
about 0.1 to about 25 wt._% of c2) a mixture of dimethicone and cyclopentasiloxane,
based on the total amount of 100 wt % emulsion C.

6. A process for hair caring comprising the following steps in sequence:
step a) applying an oil-in-water emulsion A to hair, where emulsion A has a pH value from greater than about 7.0 to about 12.0 and comprises:
a1) steartrimonium bromide, and
a2) amodimethicone;
step i) applying an oil-in-water emulsion I to the hair, where emulsion I has a pH-value from greater than about 4.0 to about 9.0 and comprises:
i1) at least one surfactant I, and
i2) at least one silicone I;
step b) washing the hair;
step c) applying an oil-in-water emulsion C to the hair, wherein emulsion C has a pH value from about 2.0 to lower than about 7.0 and comprises:
c1) behentrimonium chloride, and
c2) a mixture of dimethicone and cyclopentasiloxane, wherein the at least one silicone I may be identical with or different from a2) and c2), and step d) washing the hair.

* * * * *